United States Patent [19]

Batten

[11] 4,172,295
[45] Oct. 30, 1979

[54] TRI-CUSPID THREE-TISSUE PROSTHETIC HEART VALVE

[75] Inventor: Richard J. Batten, Yorba Linda, Calif.

[73] Assignee: Shiley Scientific, Inc., Irvine, Calif.

[21] Appl. No.: 873,049

[22] Filed: Jan. 27, 1978

[51] Int. Cl.² .............................................. A61F 1/22
[52] U.S. Cl. ......................................................... 3/1.5
[58] Field of Search ........................................ 3/1.5, 1

[56] References Cited

U.S. PATENT DOCUMENTS

| | | | |
|---|---|---|---|
| 3,714,671 | 2/1973 | Edwards et al. | 3/1.5 |
| 4,084,268 | 4/1978 | Ionescu et al. | 3/1.5 |

OTHER PUBLICATIONS

"Frame-Mounted Tissue Heart Valves: Technique of Construction," by Ivan T. Bartek et al., *Thorax,* (1974), 29, pp. 51-55.

"Mitral and Aortic Valve Replacement with Fascialata on a Frame," by W. Sterling Edwards et al., Journal of Thoracic and Cardiovascular Surgery, vol. 58, No. 6, Dec. 1969, pp. 854-858.

*Primary Examiner*—Ronald L. Frinks
*Attorney, Agent, or Firm*—Knobbe, Martens, Olson, Hubbard & Bear

[57] ABSTRACT

This invention relates to improvements in a tri-cuspid tissue prosthetic heart valve having a valve body with sewing holes provided at each interval between the cusps of the valve, which improvements are realized by the formation of the tissue from three pieces joined together at seams disposed along the intervals between the cusps of the valve.

6 Claims, 6 Drawing Figures

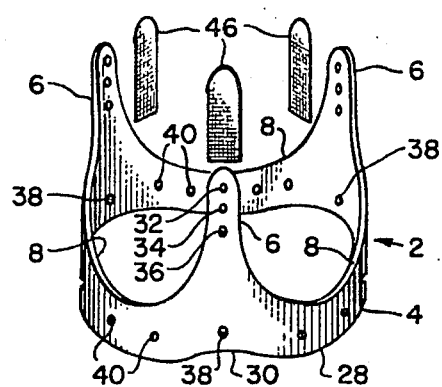
FIG. 3.
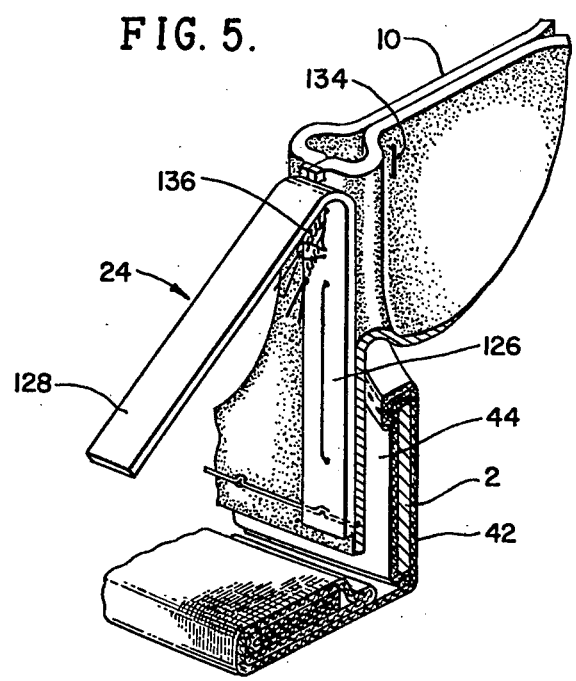
FIG. 5.
FIG. 4.
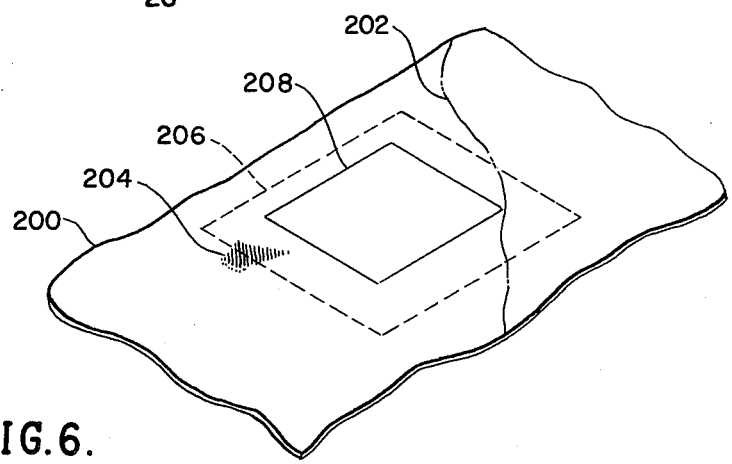
FIG. 6.

TRI-CUSPID THREE-TISSUE PROSTHETIC HEART VALVE

BACKGROUND OF THE INVENTION

Frame-mounted fascia lata heart valves were used clinically by Doctor Marion I. Ionescu and Doctor D. N. Ross in 1969. Since that time, many such valves made of autologous or hemologous fascia lata, duramater, or heterologous pericardium have been implanted. A construction of bovine pericardial valves is reported in *Frame-Mounted Tissue Heart Valves: Technique of Construction,* by Ivan T. Bartek, et al., Thorax (1974), 29, pp. 51-55.

This invention relates to an improvement in the structure and fabrication of such a valve as exemplified in the disclosure in U.S. patent application Ser. No. 679,406 now U.S. Pat. No. 4,084,268, by Doctor Ionescu and Bruce Fettel. The prior art exemplified in the above-cited application for letters patent has resulted in great success in the implantation of artificial heart valves. Nevertheless, ways to improve the construction and structure of such valves have been sought after in the art, and specifically ways to improve the structural alignment of the pericardial tissue and the valve stent and improvements which would increase the yield of usable valve tissue from animal hearts. Furthermore, improvements which would decrease the amount of stretch present in the tissue during sewing of the tissue onto the stent were sought after, along with improvements which would eliminate unsymmetrical distribution of stitching bulk on the valve.

In the prior art exemplified in the U.S. patent application Ser. No. 679,406, the valve stent or structural basis has three posts with sewing holes with which the pericardial tissue is sewn to the valve to form three cusps for a tri-cuspid valve. In this prior art, a single integral piece of pericardial tissue is used to form the tri-cuspid valve tissue surface. As is well known in the art, the three cusps must have the same configuration during opening and closing of the valve in order to achieve desirable performance characteristics of the valve. To this end, the three posts are placed 120 degrees apart, and the tissue is sewn onto the post at exactly 120-degree intervals, or at least as close thereto as possible. Thus, the critical operation in forming the three cusps is the division of the tissue used to form the valve into three equal portions comprising the circumference of the valve stent. The prior art taught that the sewing of the tissue to the stent posts would be done only after the tissue had been mounted on a conical tool or similar device with indicia located at 120-degree intervals, and marking threads sewn onto the tissue at intervals corresponding to the 120-degree displacement of the stent posts. However, in forming the vertical seam below the marker between each stent post and the tissue the prior art taught that there was no precise practical method for locating the needle hole vertically below the marker corresponding to the 120-degree interval on the tissue. Any slight error in judgement in inserting the needle into the tissue opposite the stent would result in the tissue being slightly stretched after the stitch is made with each of the sewing holes on the stent posts. Any slight stretching of the tissue on the valve would result in a slight non-uniformity among the cusps in a tri-cuspid valve. In the actual manufacture of such valves by a skilled operator, as taught by the prior art the operator would place the pericardial tissue sewn together as a cylinder over the conical tool which had on it a means for marking the tissue into three equal portions. The operator would then place a bright color marking thread on the top of the tissue corresponding to the three equally spaced marks on the tool. The operator would then place the tissue on the valve stent and align the tissue such that the three marking threads were aligned with the three stent posts on the stent. The operator would then have to visualize a vertical plumb line extending down from the marking thread on the top edge of the tissue and running parallel with the center line running through the centers of each of the sewing poles in the stent posts. It is through the imaginary plumb line that the operator would insert the needle into the tissue for sewing the tissue onto the stent. Thus, it is apparent that a great deal of human judgement is involved in correctly aligning the tissue on the stent in order to obtain a uniform tri-cuspid, geometric shape.

In the prior art, there is one stitch in the pericardial tissue forming the cylinder at which the pieces join together at two edges. When the tissue is placed onto the stent, it is oriented in such a way that the stitch between the two edges of the tissue is placed flush with one of the stent posts in order that the material in the stitch does not participate in the opening and closing movements of the tri-cuspid valve. In the prior art, there is no such stitch at the remaining two stent posts when the tissue is placed over the stent, and it is found that sewing of the tissue in the vicinity of these remaining two stents is difficult due to the wrap-around stretching action which occurs between the tissue and the stent in the absence of a seam in the tissue at the stent. Furthermore, there is greater bulk in stitching material at one stent post only, the bulk of stitching material at the remaining two stent posts being somewhat less. Therefore, the stitching bulk has an unsymmetrical distribution in the valve of the prior art.

It is well known in the art that the thickness of the pericardial tissue used to make the tri-cuspid valve must be uniform and must conform to strict dimensional tolerances. Furthermore, it is well known in the art that a successful tri-cuspid valve cannot be fabricated from pericardial tissue with blood vessels in it. Therefore, in selecting and cutting tissue from bovine animal hearts, tissue having either nonconforming thickness or blood vessels had to be cut around or rejected. This has led to a very low yield in the prior art, corresponding to one usable pericardial tissue for one valve for approximately every 100 animals so used.

SUMMARY OF THE INVENTION

According to the present invention, a solution to the problems relating to uncertainty in the alignment between the pericardial tissue and the stent posts, tension in the tissue due to wrap-around and stretching of the tissue about the stent posts during sewing, unsymmetrical distribution of stitching bulk in the valve, and the poor yield of bovine pericardial tissue usable in such valves is found through the implementation of this invention. This invention teaches the advantageous implementation of the use of three separate pericardial tissues to form a single cylindrical pericardial tissue usable to form the tri-cuspid heart valve.

The uncertainty in alignment between the pericardial tissue and the stent posts of the stent is eliminated because the tissue is divided easily into three equal portions which are then sewn together to form a cylinder.

The seams between each of the three pieces define three vertical lines in the cylinder which are then easily aligned with the three stent posts of the valve. In this way no marking thread is necessary and no conical tool is necessary in order to ascertain the proper location and alignment of the tissue on the valve stent. Also, location of the point of insertion in the pericardial tissue of the needle for sewing at each of the stent posts is greatly eased because the seam acts as a guide through which the needle may be inserted. In this way, the operator need not have to visualize an imaginary plumb line extending vertically down from the top of the cylindrical formed tissue, but instead may simply insert the needle between the two edges of the tissue at each of the three stitches joining the three pieces of tissue in a cylinder. Subsequent insertion of the needle into the sewing hole of the stent post assures perfect alignment between the pericardial tissue in each of the stent posts. This removes any uncertainty in the alignment of the tissue and the stent posts and assures accurate formation of a symmetrical tri-cuspid configuration in the tissue for the valve.

Since the tension due to the wrap-around stretching action of the tissue about each of the stent posts occurs only in the absence of a stitch between two edges of the tissue at the stent posts, this stretching is eliminated completely from the invention since there is a stitch between two edges of the pericardial tissue at each of the stent posts. This increases the ease with which the tissue may be sewn together. Furthermore, since the same type of stitch joining two edges of the pericardial tissue is present at each stent post, the stitching bulk is symmetrically distributed around the valve, thus eliminating the unsymmetrical distribution of such bulk present in the prior art valves.

Finally, because the surface area of each required piece of tissue, according to this invention, is reduced to one-third of the required area taught in the prior art, it is much easier, in cutting the tissue pieces from the bovine pericardium, to cut around defects such as blood vessels in the pericardial tissue, and nonconforming thickness of the tissue. This aspect of the invention increases the yield of usable animal pericardium for such valves from one piece of tissue for every 100 animals to approximately 15 for every 100 animals.

It would have seemed in the prior art that the use of three separate smaller tissues sewn together to form one single tissue for use in the valve would involve more steps and higher production costs. This was because it was thought that the extra step of sewing two additional seams and of having to cut an additional two rectangular sections of tissue would add to the production costs. However, it was found that the production time and production costs have not been increased with the implementation of this invention. This is due to the fact that three wedges must be cut into the tissue cylinder in order to allow the pericardial tissue to form a tri-cuspid shape when the valve is closed. Use of a single tissue to form the valve necessitates the cutting of two of the three wedges corresponding to the three posts. This step is greatly eased through the use of three tissues sewn together with the wedges already cut out. Furthermore, the step of mounting the tissue cylinder on a conical tool for the dividing and marking of the tissue into three equal segments is eliminated since the stitching of the three pieces forms three vertical lines along the cylinder which may be used instead of the marking thread to align the tissue with the stent posts. Therefore, the step of placing the tissue on the conical section and the sewing of three marking threads on the top edge of the tissue corresponding to the three stent posts is eliminated. Furthermore, this eliminates the occurrence of holes in the tissue corresponding to the sewing of the three marking threads.

In summary, a practical method has been found to improve production of prosthetic pericardial tissue heart valves which improves the accuracy of the construction of such valves, improves the yield of pericardium used in such valves, improves the symmetrical distribution of material in such valves, and facilitates and eases the sewing and the fabrication of such valves.

DESCRIPTION OF DRAWINGS

FIG. 3 is a perspective view of the stent of FIG. 2 without cloth covering;

FIG. 4 is a perspective view, partially in section, of the valve with portions removed;

FIG. 5 is a perspective view, partially in section, of a portion of a partially assembled valve; and FIG. 6 is a perspective view of a pericardial tissue used in making the valve of FIG. 1.

Referring to FIGS. 1, 2, and 3, the valve includes a thin-walled stent 2 having an annular base 4 and three equally spaced upright posts 6 with scalloped upper edges 8 on the stent between posts 6. Throughout this application the term upper will be used for convenience to refer to the outflow end of the valve and lower will be used to refer to the inflow side, recognizing that the valve may not be upright where installed. Also, the term upper edge of the stent is used to include the side edges of the posts 6. Referring now to FIG. 1 the stent supports a tissue valve element 10 which surrounds the stent and has three cusps 12, 14, and 16 meeting along their upper edge portions in the closed position. The cusps are free to separate when the pressure below the valve exceeds that above to pass blood through the valve in a known manner. The flow of blood is from bottom to top in FIG. 1 along the axis 23 of the valve.

Figure 1:
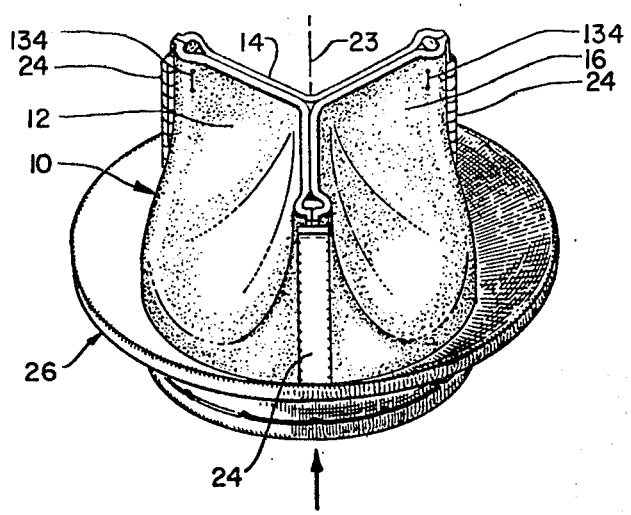
FIG. 1 is a perspective view of a completed valve.

A pledget and cover 24 extends down the outside of the tissue at each post, and a sewing ring or cuff 26 is provided for grafting the prosthetic valve into the heart valve annulus using well known surgical procedures.

Referring again to FIG. 3, the stent may be constructed of any of the known materials, suitable for cloth covered prosthetic heart valves, titanium or nickle-cobalt alloy or Teflon or Delvon plastic being among the alternatives available. Its bottom edge 28 preferably is slightly scalloped having its high points 30 beneath the posts 6. Each post 6 has sewing holes, 32, 34, and 36, three in the illustrated embodiment, spaced vertically near its upper end. Additional sewing holes 38 and 40 are spaced around the circumference of the base. In the illustrated embodiment the base 4 has one sewing hole 38 at the base of each post and five holes 40 between adjacent posts, but that number can be varied, as can the number on the posts.

The cloth covering preferably is of Dacron velour and includes an inner sleeve 42, a three-piece outer sleeve 44, and three interior post sewing pads 46, and their construction is fully disclosed in U.S. patent application Ser. No. 679,406, the disclosure of which is incorporated herein by reference.

Figure 2:
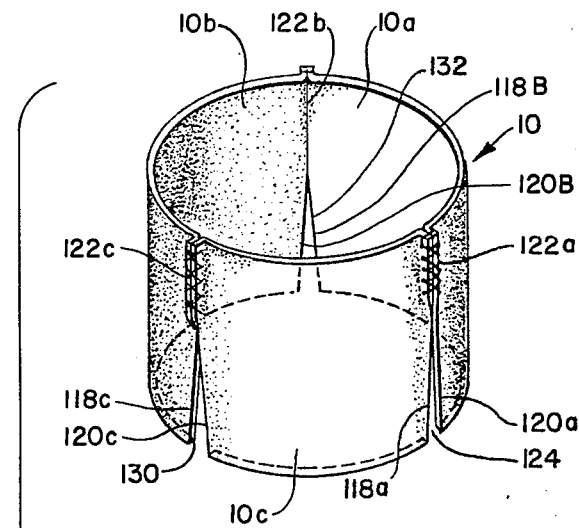
FIG. 2 is an exploded perspective view of the valve of FIG. 1 showing the cloth covered stent and the tissue covering.
Figure 2:
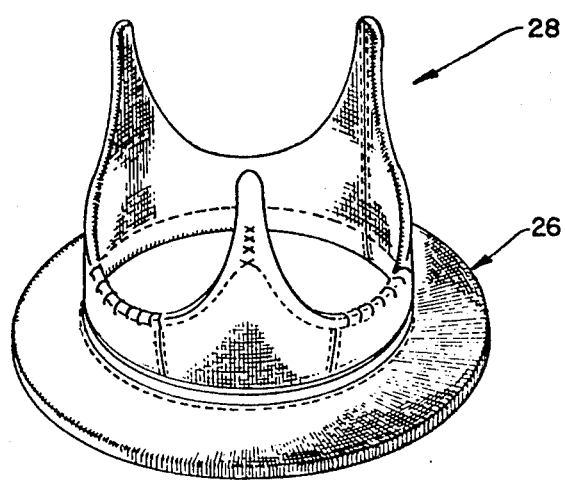

Referring now to FIG. 2, the tissues 10a, 10b, and 10c, in the exemplary embodiment bovine pericardium, are accurately cut to identical size and shape and formed into a tissue cylinder 10 of a diameter to fit over the cloth covered stent 28 as shown in FIG. 3. The top portions of the mating tissue edges 118a, 118b, 118c, 120a, 120b, and 120c are turned out face-to-face to form overcast stitched seams 122a, 122b, and 122c leaving the bottom portions of these seams 122a, 122b, and 122c temporarily unstitched, leaving a wedge 124. The tissue cylinder 10 is placed around the cloth covered stent 28 so as to circumscribe the base 4 and the posts 6 with the seams 122a, 122b, 122c centered on each post 6. A pledget and cover 24, as best shown in FIG. 5, preferably of Teflon in a form not having fibers which can unravel, is located outside the tissue 10 at each post 6. Referring now to FIGS. 4 and 5, each pledget and cover has a sewing portion 126 which lays against the tissue and continues to a cover portion 128 which covers the stitches as will be described below.

The tissue 10 and pledget 126 are attached to the stent using stitches through the upper holes 32, 34, and 36 in each post, and through the sewing portion 126 of the pledget. The stitches through the upper holes 32, 34, and 36 in each post are formed by inserting a needle with thread into the tissue as it overlays the post 6 in a location directly over each of the holes 32, 34, 36 to form the overhand stitching. Since the sewing holes are not visible, their location cannot be precisely ascertained before insertion of the needle into the tissue, and therefore the alignment of the tissue with the holes in each post is critical. In the prior art, there was no seam in the tissue at two of the posts, and therefore the insertion of the needle into the tissue was located with some uncertainty at those posts where there was no seam in the tissue. However, in this invention, the seams themselves, 122a, 122b, 122c, serve to divide the tissue into 120-degree portions, corresponding to a location of the sewing holes in each of the three posts, and thereby serve as guides through which the needle and thread may be inserted to precisely locate each seam 122a, 122b, 122c, over the sewing holes 32, 34, 36 in each of the three posts 6. In the prior art, as exemplified in U.S. Pat. application Ser. No. 679,406, there was no guide through which the needle could be inserted in order to accurately align the stitching with the sewing holes 32, 34, 36. The presence of the seams 122a, 122b, 122c at each and every one of the three posts 6 eliminates the uncertainty in the location of the stitching on the tissue 10 along the circumference of the stent. This greatly improves the accuracy of the alignment of the tissue 10 on the stent 2, and thereby improves the uniformity of the cusps 12, 14, 16 formed by the tissue when the valve is in the closed configuration. Small wedges 124, 130, and 132 are located at the bottom portion of the tissue at the three posts 6 to provide relief to permit the tissue to close in cusps.

The tissue valve is tucked around each individual post 6 by stitches 134 as shown in FIG. 4. This causes the tissue valve to close in three cusps 12, 14, and 16 as shown in FIG. 1. Each end 136, and 137 of the thread extends from the tuck stitch 134 through the inner sleeve, the inner post sewing pad, the upper hole in the stent, three layers of cloth in the outside of the post, the tissue outside the post, and the sewing portion of the pledget and are tied off as shown at 136 in FIGS. 4 and 5. The pledget and cover 24 is not shown in FIG. 4 in order to more clearly show the other details.

The seams 122a, 122b, 122c play a role in facilitating the ease with which the stitches 134 are sewn. In the prior art, two of the posts 6 did not have seams 122b and 122c at the posts. At these posts 6 without seams 122b, 122c, the tissue wrapped tightly around the back of the posts 6 on the opposite side of the posts from the tuck stitch 134, thereby increasing the tension at the tuck stitch 134. This tension increases the difficulty with which the tuck stitch 134 must be sewn. According to the present invention, there is a seam 122a and 122b and 122c at each post 6. Each seam 122a, 122b, 122c substantially reduces the tension at the tuck stitch 134 and the tissue 10 because the edges of the tissue at each seam face away from the post 6. This improves the ease with which the tuck stitch may be formed, and thereby improving the fabrication of the valve. Furthermore, since there is a seam 122a, 122b, 122c at each post 6, each pledget 24 now extends the same amount of distance away from the tissue 10 in order to accommodate the stitching of the seam 122a, 122b, 122c. This was not true in the prior art since only one post 6 had a seam 122a and the pledgets 24 at each post 6 did not extend an equal distance from the tissue 10, giving rise to unsymmetrical distribution of bulk in the valve. The implementation of this invention ensures a symmetrical configuration of the pledgets 24 at each of the posts 6. As is taught in this art, a symmetrical distribution of bulk on a prosthetic heart valve is preferable to an unsymmetric distribution of bulk.

The reason for the increase in yield of pericardial tissues from animal hearts is apparent in FIG. 6. The pericardial tissue derived from the bovine animal heart is shown at 200, and at 202 is a blood vein passing through the pericardial tissue 200. The shaded area 204 represent an area of non-uniform and nonconforming thickness in the tissue 200. The dashed lines 206 represent the size of pericardium that must be cut in order to form a valve according to the prior art. 208 represents the size of the pericardium required according to the present invention, which is approximately one-third the area of the pericardium cut-away of 206. As apparent in FIG. 6, the prior art could not obtain a usable pericardium from this particular tissue 200, but according to the present invention, the cut-away area 208, which successfully avoids the blood vein 202 and the non-uniform thickness area 204 results in a usable piece of pericardium from the tissue 200. It is this particular feature which has resulted in a 15-fold increase in the yield of usable pericardium from bovine animal hearts according to the present invention.

In summary, it is seen that the implementation of this invention results in improvement in the accuracy of alignment of the tissue and the valve stent, thereby improving the formation of a tri-cuspid shape, improvement in the yield of animal tissue usable for making such valves, reduction of tension in the tissue impeding the sewing of the tuck stitch 134, and a more symmetrically distributed stitching bulk across the valve. This invention may be similarly implemented for valves having more than three posts and cusps by providing seams in the pericardial tissue at each stent post for any number of stent posts. In this way, three pieces of tissue are used to make a tri-cuspid valve having three posts, four pieces of tissue are used to make a four-cuspid valve having four posts and so on.

I claim:

1. A method for improving the alignment of tissue on a multi-cusp tissue prosthetic heart valve frame, comprising;
   forming stitch receiving apertures through said frame corresponding to the boundaries between cusps in said valve;
   obtaining the tissue used to form the valve cusps of said valve from a plural number of tissues corresponding to the number of cusps of said valve;
   joining said plural tissues into one piece by sewing seams between each of said plural tissues forming a juncture at each of said seams; and
   precisely aligning said one piece of tissue onto the body of said valve by inserting a needle through each of said junctures and through each of said stitch receiving apertures in said frame.

2. The method of claim 1 further comprising a tuck stitch in said tissue proximal each of said set of sewing holes and disposed opposite said seam adjacent said set of sewing holes.

3. A multi-cusp prosthetic heart valve formed of tissue comprising:
   a frame;
   a plural number of sets of sewing holes extending through said frame at each of the boundaries between the cusps of said valve;
   a plural number of tissue pieces corresponding to the number of said cusps;
   a plural number of seams joining said tissue pieces into a single piece, forming thin juncture lines between adjacent tissue pieces; and,
   thread stitched through said juncture lines and through each adjacent set of sewing holes through said frame.

4. The heart valve defined in claim 3 further comprising a tuck stitch in said tissue proximal each of said seams.

5. A multi-cuspid prosthetic heart valve comprising:
   a frame having sewing holes provided therein;
   a plural number tissues equal to the number of cusps of said valve;
   a plural number of seams joining each of said tissues into one piece of tissue; and
   thread passing through said seams and through sewing holes in said rigid frame.

6. The prosthetic heart valve defined in claim 5 wherein said plural number of cusps is equal to 3.

* * * * *